United States Patent [19]
Wicki

[11] Patent Number: 5,157,810
[45] Date of Patent: Oct. 27, 1992

[54] APPARATUS FOR MEASURING THE MASS OF A SLIVER

[75] Inventor: Raphael Wicki, Aadorf, Switzerland

[73] Assignee: Maschinenfabrik Rieter AG, Winterthur, Switzerland

[21] Appl. No.: 692,714

[22] Filed: Apr. 29, 1991

[30] Foreign Application Priority Data

Apr. 27, 1990 [CH] Switzerland ............... 01439/90
Apr. 27, 1990 [CH] Switzerland ............... 01440/90

[51] Int. Cl.$^5$ ............................................. D01H 5/32
[52] U.S. Cl. .................................... 19/240; 19/0.23; 19/106 R; 19/260; 73/160
[58] Field of Search ............. 19/0.23, 0.24, 106 R, 19/239, 240, 257, 258, 260; 73/159, 160

[56] References Cited

U.S. PATENT DOCUMENTS

| | | | |
|---|---|---|---|
| 3,314,114 | 4/1967 | Wyatt | 19/240 |
| 3,827,106 | 8/1974 | Varga | 19/240 |
| 3,938,223 | 2/1976 | Grice | 19/240 |
| 3,977,046 | 8/1976 | Wise | 19/240 |
| 4,100,649 | 7/1978 | Erismann et al. | 19/240 |
| 4,266,324 | 5/1981 | Hasegawa et al. | 19/239 |
| 4,539,729 | 9/1985 | Meile et al. | 19/258 |
| 4,646,387 | 3/1987 | Oswald et al. | 19/0.23 |

FOREIGN PATENT DOCUMENTS 0078393 5/1983 European Pat. Off. .
0192835 9/1986 European Pat. Off. .
3826861 3/1989 Fed. Rep. of Germany .

*Primary Examiner*—Werner H. Schroeder
*Assistant Examiner*—Michael A. Neas
*Attorney, Agent, or Firm*—Sandler, Greenblum & Bernstein

[57] ABSTRACT

For use in a spinning mill, the apparatus is used to even up the mass of sliver being conveyed, for manufacturing perfect roving yarns. The evening up takes place by measuring the thickness of the sliver after it has been compressed to a certain volume in a gap between two rollers. One roller is rigidly arranged, whereas the other is supported in a resilient manner or has a resilient portion. Movements by the resilient roller are indicative of the extent of the deviations in the thickness of the conveyed sliver, and the movements of the resilient roller are monitored by a sensor which sends signals for controlling devices for facilitating the evening up the amount of the sliver mass being fed. By means of the arrangement of rollers, the apparatus does not generate oscillations which would alter the measured results from the measuring rollers under certain operational conditions. The measuring apparatus is arranged from a constructional point of view in such a manner that its natural oscillations are such that it provides precise measured values under all operational conditions. In addition, the material is easily fed into the measuring device.

28 Claims, 3 Drawing Sheets

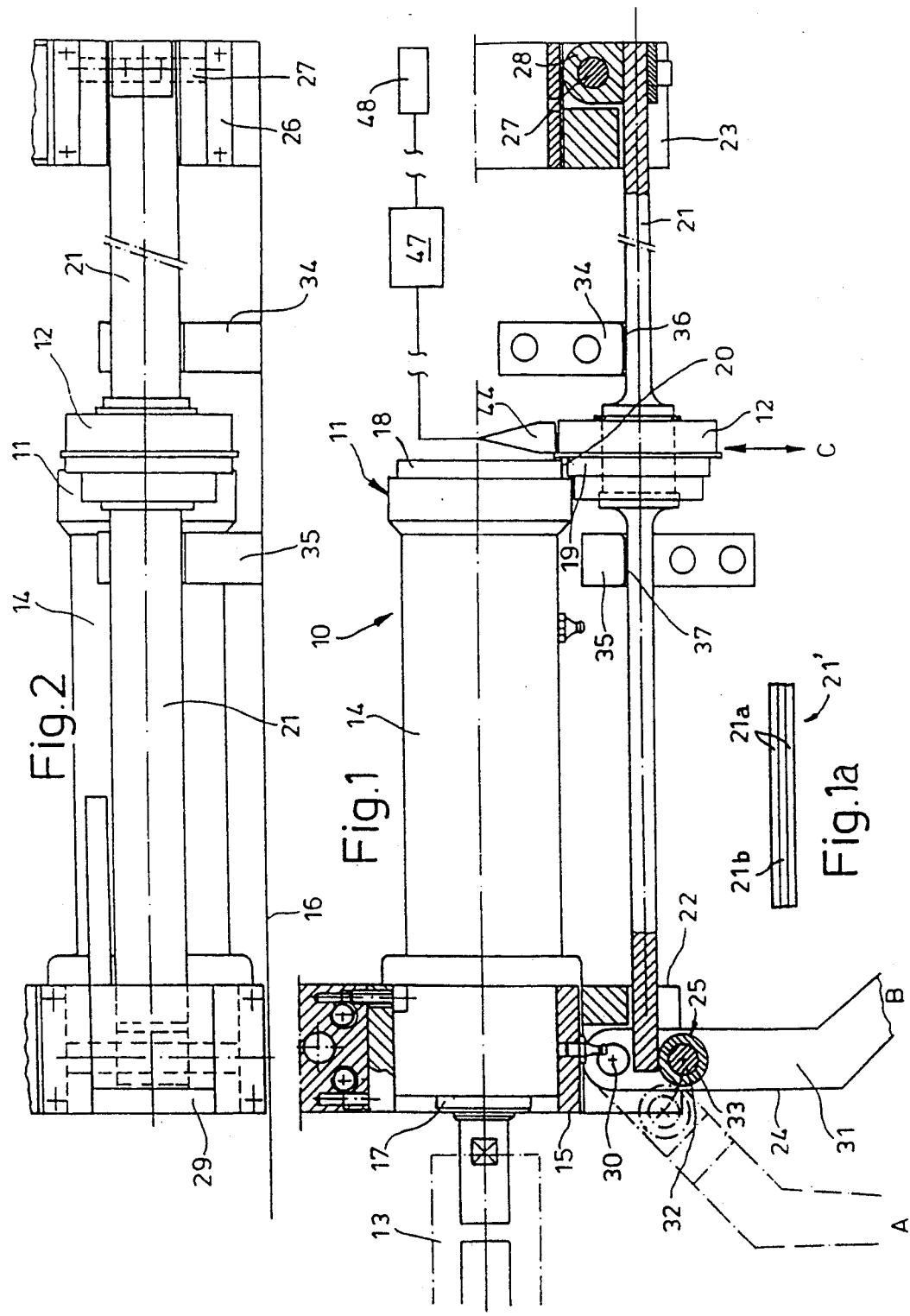

APPARATUS FOR MEASURING THE MASS OF A SLIVER

BACKGROUND OF THE INVENTION

1. Field of the Invention

The invention relates to an apparatus for the continuous measurement of the mass of a continuously conveyed sliver for the purpose of evening up the sliver.

2. Description of Background and Other Information

In the field of spinning processes, it is the function of the drawing device of a drafting frame, for example, to "even up" a sliver before manufacturing a roving yarn from such a prepared sliver. The evening up takes place by the doubling of several slivers and by changing or regulating the speed of the rollers conveying the slivers in a drafting area of the drawing device of a drafting frame, or by changing the speed of feed rollers at the entrance of a carding machine which produces slivers. If the mass of a continuously conveyed sliver either exceeds or falls below a predetermined value, such deviations are compensated for by changes in the conveyance speed for providing either more or less drafting for the evening up.

The changes in the conveyance speed are made by means of a measuring apparatus and a control device cooperating with the measuring apparatus, whereby the control device is provided for effecting appropriate changes in the speed of the roller drives. To this effect, the sliver is compressed in the measuring apparatus to a predetermined extent and the thickness of the thus formed volume is measured, whereby deviations from a predetermined desired thickness, identifying the evening up, generate signals for the control devices.

A measuring apparatus having the above-mentioned function is known which, with regard to its axle bearings, consists of a stationary driving roller and a movable carrier roller which, between them, form a roller slit which is variable with regard to its dimension. The driven driving roller and the carrier roller, which is driven by way of friction, are both arranged as step rollers which are both engaged in such a manner that a roller slit is formed in the direction of the sliver's movement, which is open in the direction of movement, but is otherwise limited by the rollers' circumferences and the steps, whereby the sliver is compressed for the purpose of measuring the thickness of the sliver when the sliver passes between the rollers.

The carrier roller's axle bearings are provided by means of leaf springs attached to an anchoring in such a manner that the axle bearings may perform parallel movements. Furthermore, springs act upon the axle bearings of the carrier roller, the forces of which are adjusted such that the carrier roller is pressed onto the driving roller with a predetermined pressure. In the event of changes in the compressed sliver volume caused by an accumulation of mass, the roller slit either extends or closes under a pendulum displacement of the axle position of the carrier roller, whereby the amount of the pendulum displacement is monitored by a sensor for generating control signals.

The known apparatus constitutes an oscillating body in which natural oscillations, which are subsidingly dampened in operation, superimpose with excitation oscillations caused by the movements of the carrier rollers. Due to the construction of this arrangement, particularly due the forces of inertia of its oscillating masses, i.e., deflecting forces and the damping resistance of its components and the effect of the exterior excitation forces caused by the carrier roller, the apparatus falls into an oscillatory behavior with natural frequencies under special operational conditions, which lead to the fact that the results of the measurements of the apparatus are altered, thus resulting in insufficiently evened up slivers. In addition, in the known apparatus, the initial section of a new sliver is very difficult to introduce between a driving and carrier roller and requires considerable efforts to do so.

SUMMARY OF THE INVENTION

Starting from the perspective of the aforementioned known apparatus, the inventor has undertaken the objective of creating an apparatus with measuring rollers, including their function, known from the state of the art described above, whereby the apparatus, in addition to simplifying and facilitating the introduction of the sliver, is arranged from a constructional point of view in such a manner that, under all operational conditions, the oscillatory behavior of the apparatus only allows natural oscillations to arise in those frequency ranges which do not alter the results of the measurements by the measuring rollers, whereby the objective is solved in accordance with the present invention.

By the arrangement in accordance with the invention, the measuring apparatus comprises, when in operation, natural oscillations in frequency ranges which do not alter the results of the measurement.

Accordingly, the present invention comprises an apparatus for monitoring the mass of a conveyed sliver, the apparatus including:

a driving roller rotatable about an axis of rotation, the driving roller having a predetermined peripheral portion;

a carrier roller rotatable about an axis of rotation and positionable in a driven position with the driving roller, the carrier roller having a predetermined peripheral portion, whereby, in the driven position of the driving roller, a slit is formed between the predetermined peripheral portion of the driving roller and the predetermined peripheral portion of the driven roller through which the sliver is conveyed;

a carrier upon which the carrier roller is mounted, the carrier including a carrier portion extending from each side of the carrier roller in a direction of the axis of rotation of the carrier roller;

means for restraining each of the carrier portions from movement in a direction away from the axis of rotation of the driving roller; and means for sensing deflections of at least a portion of the carrier roller during conveyance of the sliver.

According to a particular aspect of the invention, the means for restraining each the carrier portion further includes means for facilitating movement of both the carrier and the carrier roller toward or away from the axis of rotation of the driving roller, thereby facilitating movement of the carrier roller into or out of the driven position, respectively.

In a preferred embodiment of the invention, each of the carrier portions has a thickness and a width, the width being defined by a side generally facing the rotational axis of the driving roller, whereby each of the carrier portions has a greater tendency to deflect in a direction away from the rotational axis of the driving roller, under the influence of a relatively thickened section of the conveyed sliver, than in other directions.

In an alternative embodiment of the invention, the carrier roller has a resilient portion bordering the slit, the resilient portion being deflectable under the influence of a relatively thickened section of the conveyed sliver.

In a more comprehensive embodiment, the present invention further includes a drafting frame having conveying rollers, and means for controlling the speed of the conveying rollers in response to signals generated by the means for sensing deflections.

Alternatively, the present invention further includes a carding machine having feed rollers, and means for controlling the speed of the feed rollers in response to signals generated by the means for sensing deflections.

In a more specifically defined embodiment, the invention includes:

a driving roller rotatable about an axis of rotation;

a carrier roller positionable in a driven position with the driving roller, the carrier roller having a plurality of circumferential stepped surfaces, whereby a roller slit is defined between the driving roller and the carrier roller, through which the sliver is conveyed, the roller slit being enclosed;

a carrier upon which the carrier roller is mounted; means for selectively restraining at least a portion of the carrier from movement, thereby positioning the carrier roller in the driven position with the driving roller, and facilitating movement of both the carrier and the carrier roller toward or away from the axis of rotation of the driving roller, thereby facilitating movement of the carrier roller into or out of the driven position; and a sensor for sensing deflections of at least a portion of the carrier roller in response to variations in the mass of the continuously conveyed sliver.

According to a particular aspect of the invention, the carrier is rectangular in a transverse cross-section and, in a direction of a vertical area of cross-section, has a higher moment of inertia than in a direction of a horizontal area of cross-section.

In a further aspect of the invention, the means for selectively restraining at least a portion of the carrier for movement and facilitating movement of both the carrier and the carrier roller includes at least two spaced-apart support bearings for supporting spaced-apart portions of the carrier, the carrier roller being arranged between the support bearings.

In a more detailed feature of the invention, the support bearings of the carrier include a swivelling bearing for holding a first portion of the carrier and being formed by a pin within a hinge body, and a swivelling lever and an abutment thereon, the swivelling lever being journalled for movement including means for enabling the lever to move from a first position, in which the abutment engages the carrier for maintaining the carrier roller in the driven position, and a second position, in which the abutment is disengaged from the carrier, thereby permitting movement of the carrier roller out of the driven position. Preferably, the swivelling bearing has a rotational axis which extends parallel to a perpendicular line through the roller slit.

In one form of the invention, the carrier includes a metallic carrier element extending on either side of the carrier roller, each the metallic carrier element having a rectangular cross-section.

In one embodiment of the invention, the carrier is included of a synthetic material, preferably a fiber-reinforced synthetic material.

In a further embodiment, the carrier includes layers of carrier elements, the layers of carrier elements including at least one metallic carrier element layer and at least one non-metallic carrier element layer, the latter preferably being a fiber-reinforced synthetic material.

According to a further aspect of the invention, on both sides of the carrier roller, respective end stops are provided which are engageable with portions of the carrier facing the driving roller.

In a particular embodiment of the invention, the carrier roller includes a running sleeve having a small mass, the sleeve being rotatably held by a journal bearing on a section of a shaft connected to the carrier.

In one form of this embodiment, the running sleeve includes recesses extending in an axial direction of the running sleeve. It is contemplated that a material for damping vibrations can be provided within the recesses in the running sleeve. This material can be plastic or rubber.

In an alternative embodiment of the invention, the carrier roller includes means for providing resilient-mounted eccentric rotation around a rotational axis.

More specifically in this embodiment, the carrier roller includes an inner ring and a running sleeve positioned exteriorly of the inner ring, the running sleeve having an intermediate layer included of a resilient material, whereby the inner ring is mounted to the carrier by means of a journal bearing. The material of the intermediate layer can include a material having a high internal damping.

Further, regarding this alternative embodiment, the carrier includes cross-sectional dimensions such that, in the event of an application of force on the carrier caused by a displacement of the running sleeve relative to the journal bearing, the carrier remains generally free from deflection.

BRIEF DESCRIPTION OF THE DRAWINGS

The above and additional objects, characteristics, and advantages of the present invention will become apparent in the following detailed description of preferred embodiments, with reference to the accompanying drawings which are presented as non-limiting examples, in which:

FIG. 1 shows an embodiment of the apparatus in accordance with the invention in a top view, partially in section;

FIG. 1a shows, in a partial top view, an alternate embodiment of the carrier of FIG. 1;

FIG. 2 shows a side view of the apparatus, in accordance with FIG. 1;

DETAILED DESCRIPTION OF PREFERRED EMBODIMENTS

Figure 3:
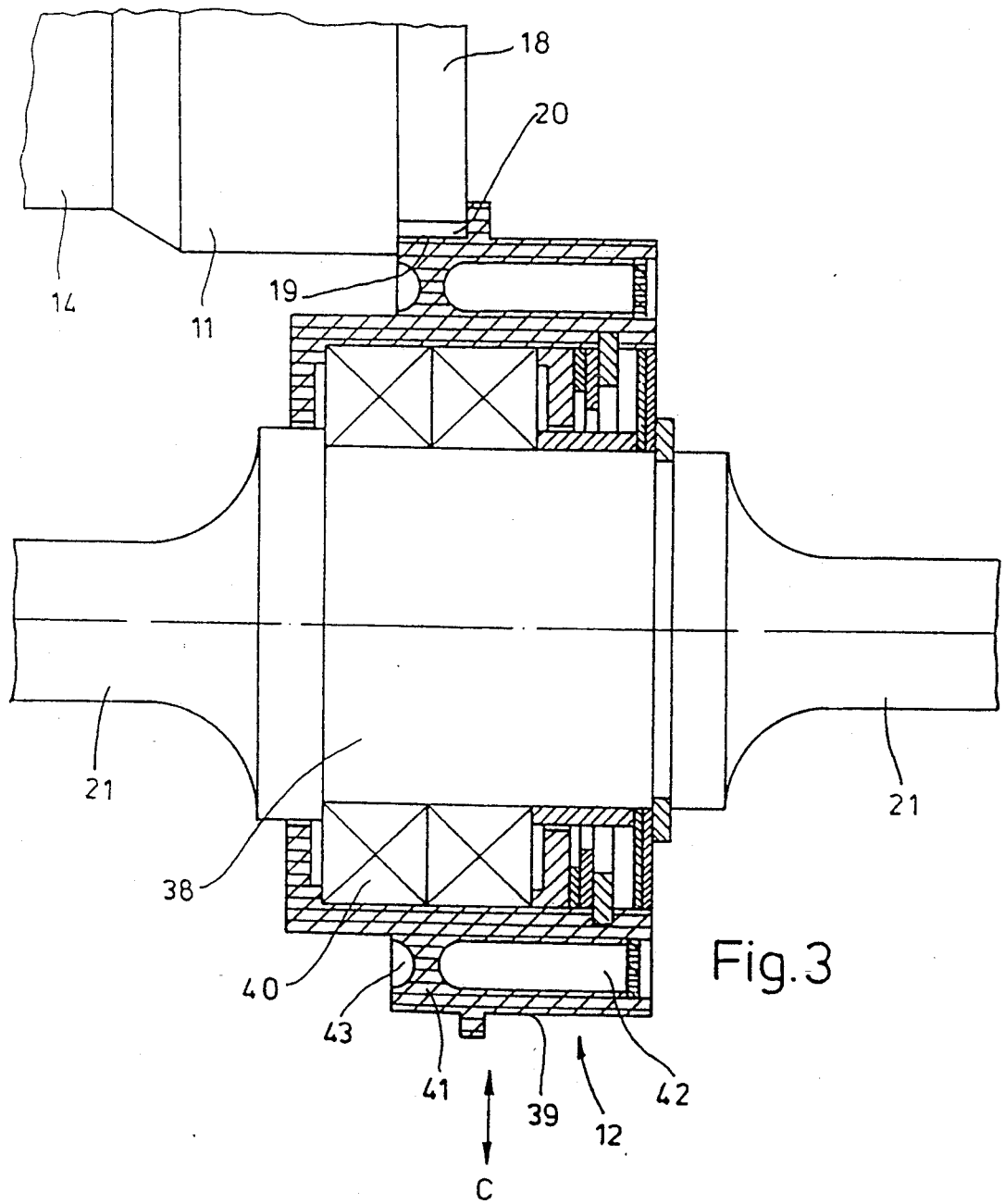
FIG. 3. shows a partial view of the pair of rollers in accordance with FIG. 1 in a top view, whereby one of the rollers is shown in section.

With regard to the following description, the drawings illustrate the invention in sufficient detail to enable one of ordinary skill in the art to make and use the invention, whereby certain details generally known to those of ordinary skill in the art may have been omitted or simplified for the sake of clarity in the following description of the preferred embodiments of the invention.

In accordance with FIG. 1, the measuring device 10 in accordance with the invention includes a pair of rollers, namely, a driving roller 11 and a carrier roller 12. The driving roller 11 is rotatably driven by a drive member 13, the drive member being suitably connected to, and driven by, a motive power source, whereby the carrier roller 12 is caused to rotate by frictional engagement of a portion of the carrier roller with a portion of the driving roller 11.

The driving shaft 17 of driving roller 11 is held in a cylindrical sleeve 14 in a known manner, the sleeve being held on one side in a bearing block 15. The bearing block 15 is attached to a base plate 16, shown in the side view of FIG. 2. Driving roller 11 is held free from play in the radial direction as well as the longitudinal direction by the respective bearings of its driving shaft 17 in the sleeve 14.

The arrangement of the receiving part of sleeve 14 in the bearing block 15 further ensures a rigid bearing of sleeve 14 so that the over-mounted driving roller 11 rotates in a stationary axle position, viz., stationary in the aforementioned radial and longitudinal directions. The stationary position of the axis of rotation of the driving roller 11 is important for the function of the measuring apparatus, to be further described below, in that a circumferential part of the driving roller 11 serves as a fixed point of reference for the measurement.

The driving roller 11 and the carrier roller 12 are preferably arranged as so-called "step" rollers. The step 18 of the driving roller 11 engages with step 19 of the carrier roller 12 in such a manner that a roller slit 20 arises, through which the sliver extends, the roller slit being open in the direction of the movement of the sliver, but otherwise closed on all sides and thus forming, in a horizontal cross-section, a square or rectangular cross-section which is limited, or enclosed, on all sides. Alternatively, it is conceivable that other roller profiles could be provided for providing a roller slit between corresponding portions of the driving roller and carrier roller. For example, either or both of the rollers 11, 12 could have a peripheral concavity, the latter configuration providing a generally rounded slit.

The carrier roller 12 is arranged along the length of a carrier 21, in the center of the carrier or otherwise, the carrier having portions held on both sides of the roller 12 in support bearings 22, 23, whereby the support bearings 22, 23 are connected with base plate 16. The carrier 21 may comprise a rectangular cross-section and is arranged in such a manner that, as shown, a longer side of the rectangular cross-section extends vertically, or substantially vertically, and the shorter side extends horizontally, or substantially horizontally. The dimensions of the cross-section are selected such that the carrier 21 comprises a far greater moment of inertia in the vertical direction than in the horizontal direction, so that the carrier 21 deflects under the influence of a load only in the horizontal direction, but not in the vertical direction.

Such dimensioning of the carrier 21 is preferable in the event that the carrier roller 12 is arranged for performing a resilient eccentric rotation around its axis of rotation, described further below with regard to FIG. 4, for example. In the event that the carrier roller is arranged for performing a resilient eccentric rotation around its axis of rotation, the carrier 21 may have any kind of shape in cross-section, whereby, however, the carrier 21 is to be dimensioned in such a manner that in the event of an application of force on the carrier caused by the displacement of the running sleeve 39 relative to its journal bearing 40 and acting upon the center of the carrier, the carrier 21 remains free from deflection, i.e., it is to be regarded as rigid within the scope of the forces acting upon it.

The carrier 21 may be made from a metallic or non-metallic material. Steel may be used as a metallic material and synthetic material may be used as a non-metallic material, preferably a fiber-reinforced synthetic material. As shown in FIG. 1a, carrier 21 may also be constructed from layers of metallic and non-metallic carrier elements 21a, 21b, for example. This construction, i.e., a carrier comprised of an arrangement of layers of metallic and non-metallic carrier elements may also be advantageous. For example, the carrier 21' arranged in layers has the advantage that, by using different element materials, the damping behavior of carrier 21 can be respectively modified. In this embodiment, the layers of metallic and non-metallic materials can be layers of steel and synthetic materials, the synthetic material being a fiber-reinforced material, for example. Similarly, elastomeric materials are also contemplated as the non-metallic material. In addition, the number of layers can be varied, if desired.

The bearing 23 of the carrier 21 is arranged as a pivot bearing. The bearing 22 is arranged as a lever means 24 with an abutment 25. The bearing 23 comprises a cylindrical pin 27 with a hinge body 28 rotatable around the pin, whereby the pin is held vertical, or generally vertical, to base plate 16 in a bearing block 26. Carrier 21 is connected with the hinge body 28 and thus swivels around pin 27.

Bearing 22 comprises bearing block 29 connected with base plate 16, the block 29 comprising a vertically extending round turning pin 30 around which the lever means 24 turns. The lever means 24 comprises a lever arm 31 which carries the abutment 25 on its side facing the base plate 16, the abutment being formed by a sleeve 33 rotatable around a pin 32.

FIG. 1 shows the lever arm 31 in the two swivelling positions A and B, position A being shown in phantom lines. For movement to the swivelling position A, the carrier 21 is swivelled around pin 27, whereas in the swivelling position B, the longitudinal axis of carrier 21 is kept parallel to the axis of rotation of the driving roller 11. On both sides of the carrier roller 12, end stops 34 and 35 are provided on base plate 16. On the bearing surfaces 36 and 37 of the stops, the side of the carrier 21 facing the driving roller 11 is stopped, whereas the sleeve 33 of abutment 25 is stopped on the side opposite of the aforementioned side in the closing position of the lever means 24. Therefore, carrier 21 is deflectably held in the direction of movement C in the event of a concentrically rotating running sleeve 39 of carrier roller 12, shown in FIG. 3, for example, and not deflectably held in the event of an eccentrically rotatable sleeve 39 of carrier roller 12, shown in FIG. 4, for example.

FIG. 3 shows a part of the driving roller 11 and a sectional view of the carrier roller 12, arranged in accordance with a preferred embodiment of the invention. The carrier roller 12 rests on a round section of the shaft 38, the shaft otherwise being part of the rectangular carrier 21. The shaft section 38 can be either unitary with the carrier 21 or integral therewith by being welded thereto, for example. The carrier roller 12 is formed by a running sleeve 39 which turns around the section of shaft 38 by means of a journal bearing 40, e.g., in the form of spindle bearings. Running sleeve 39 is arranged on the journal bearing 40 so that it cannot move, or so that it cannot substantially move, in the axial direction of the section of shaft 38, by means known in the bearing art.

In order to provide the running sleeve 39 with the smallest possible mass, the ring-like sleeve 41 of running sleeve 39 is arranged with recesses 42, 43 extending in the axial direction of the sleeve.

Figure 4:
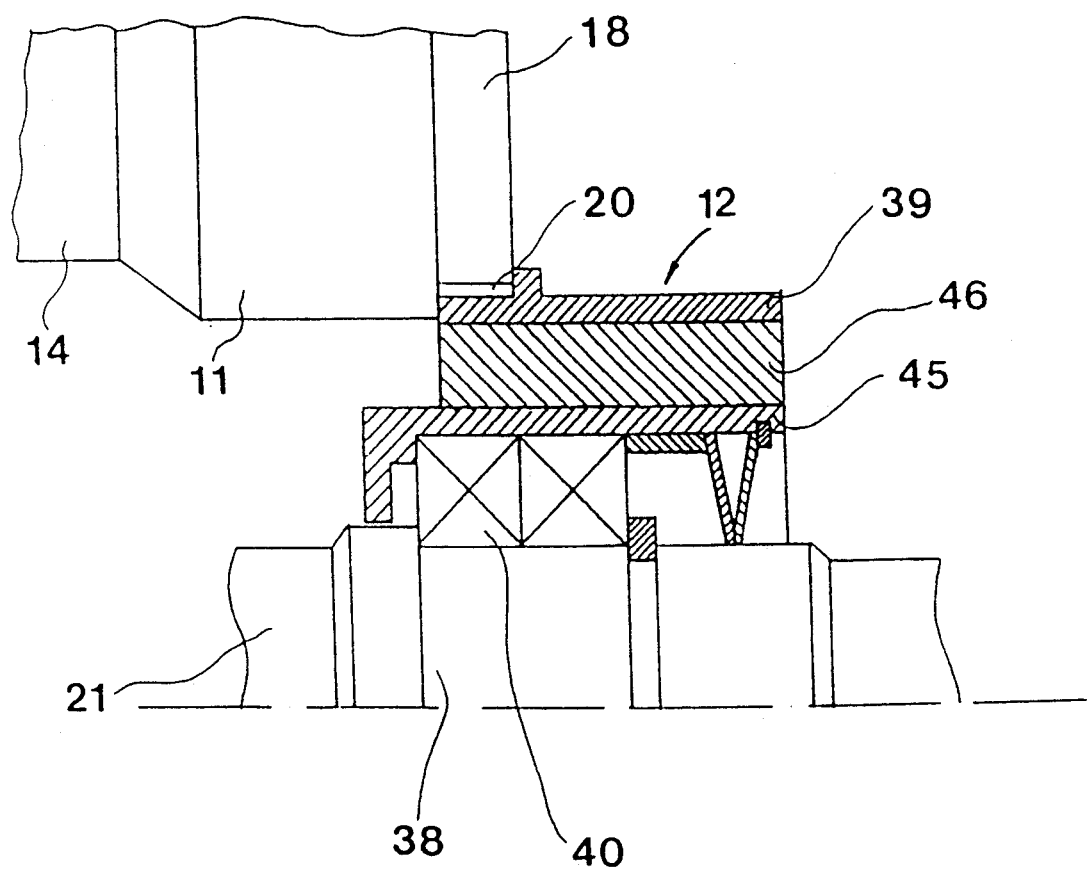
FIG. 4. shows a partial view of the pair of rollers in a further embodiment in a top view, whereby one of the rollers is shown in section.

FIG. 4 shows a part of the driving roller 11 and a section through a further carrier roller 12 in accordance with a further preferred embodiment of the invention. The carrier roller 12 of this embodiment is also held on a round section of a shaft 38 which is also part of, or attached to, the carrier 21. The carrier roller 12 is formed by a running sleeve 39 and an inner ring 45 which rotate around the section of the shaft 38 by means of journal bearing 40, e.g., in the form of spindle bearings. Running sleeve 39 and the inner ring 45, the ring being engaged with the journal bearing 40, are arranged on the journal bearing 40 in such a manner that they cannot perform any movements in the axial direction of the section of shaft 38.

Between the running sleeve 39 and the inner ring 45, which are both made, preferably, from a metallic material such as steel, there is an intermediate layer 46 made from a non-metallic, resilient material, preferably rubber or a silicone caoutchouc. Due to their high natural damping, rubber or silicone caoutchouc are the preferred resilient materials for the intermediate layer. It is the purpose of the intermediate layer 46, on the one hand, to provide a slip-free connection between the running sleeve 39 and the inner ring 45 in the direction of the carrier roller 12 and, on the other hand, to bring about a rotation of the running sleeve 39 around the inner ring 45 which is displaced between the running sleeve 39 and the inner ring 45 (i.e., eccentric rotation) for the purpose of achieving the inventive function of the carrier roller 12, whereby the high natural damping of the material of the intermediate layer 46 only allows vibrations of the apparatus in frequency ranges which do not have an adverse effect on measured values obtained from driving roller 11 and carrier roller 12. In this type of embodiment, i.e., in which the carrier roller includes a damping material, although the carrier 21 can be constructed as described above with regard to the first embodiment described, the carrier can be formed of any other construction since the deflection of the carrier 21 is not essential, the deflection of the running sleeve 39 itself providing the necessary movement to be sensed.

The operation of the measuring apparatus in accordance with the invention is as follows:

By moving the lever means 24 to the swivelling position A, and withdrawing the abutment 25 from engagement with the carrier 21, the carrier 21 is unlocked and can be swivelled around the cylindrical pin 27, so that by moving the carrier roller 12 away from the driving roller 11, the roller slit 20 is opened. After inserting a sliver into the open roller slit 20, the slit is closed again by moving the lever means 24 back into swivelling position B to lock the carrier 21 by means of the engagement of the abutment 25 with the carrier 21. In such a manner, the sliver is compacted, by pressing out the air contained within the sliver, to a volume pursuant to the dimension of the roller slit. The driving roller 11 is made to turn by means of drive member 13 and, via the resulting friction, drives carrier roller 12 so that the sliver is conveyed through the roller slit under continuous compaction.

During the conveyance, the carrier roller 12 enables the sensing of changes in the amount of the mass of the sliver by measuring the thickness of the compressed volume in roller slit 20. Pertinent changes in the thickness, such as increases in the thickness, cause the carrier 21 to deflect in the direction of movement C (in the arrangement of the carrier roller 12 according to FIG. 3) or cause an eccentric movement of running sleeve 39 (in the arrangement of the carrier roller 12 according to FIG. 4), thus opening the roller slit 20 by the moving off of carrier roller 12 from the driving roller 11. The change in the position of the carrier roller 12, which is equivalent to the deflection of carrier 21, or that which is equivalent to the eccentric movement of the running sleeve 39, is registered on the periphery of the sleeve 39 of the carrier roller 12 by means of a sensor 44, preferably by way of a touch-free measurement of distance, or by detection of the magnitude of the deflection above a predetermined threshold distance, whereby the sensor emits signals, by means of devices well-known in the art for such purposes, to appropriate control means 47 for causing changes in the speed of the conveying rollers in the drafting frame or changes in the speed of the feed rollers of a carding machine, each of which is schematically depicted in FIG. 1 by reference numeral 48.

The measuring apparatus 10 in accordance with the invention are described above in connection with a carding machine or a drafting frame for the purpose of evening up a sliver. However, their use is not limited to the above application. They may also be used with other textile machines in which measurements of slivers or yarns are to made.

Further, although the invention has been described with reference of particular means, materials and embodiments, it is to be understood that the invention is not limited to the particulars disclosed and extends to all equivalents within the scope of the claims.

What is claimed is:

1. In an apparatus for continuous measurement of the mass of a continuously conveyed sliver, said apparatus comprising:

a driving roller rotatable about an axis of rotation;

a carrier roller positionable in a driven position with said driving roller, said carrier roller having a plurality of circumferential stepped surfaces, whereby a roller slit is defined between said driving roller and said carrier roller, through which said sliver is conveyed, said roller slit being enclosed;

a carrier upon which said carrier roller is mounted, said carrier being rectangular in a transverse cross-section and, in a direction of a vertical area of cross-section, having a higher moment of inertia than in a direction of a horizontal area of cross-section;

means for selectively restraining at least a portion of said carrier from movement, thereby positioning said carrier roller in said driven position with said driving roller, and facilitating movement of both said carrier and said carrier roller toward or away from said axis of rotation of said driving roller, thereby facilitating movement of said carrier roller into or out of said driven position; and a sensor for sensing deflections of at least a portion of said carrier roller in response to variations in the mass of said continuously conveyed sliver.

2. The apparatus of claim 1, wherein:
said means for selectively restraining at least a portion of said carrier for movement and facilitating movement of both said carrier and said carrier roller comprises at least two spaced-apart support bearings for supporting spaced-apart portions of said carrier, said carrier roller being arranged between said support bearings.

3. The apparatus of claim 1, wherein:
said carrier comprises:
a metallic carrier element extending on either side of said carrier roller, each said metallic carrier element having a rectangular cross-section.

4. The apparatus of claim 1, wherein:
said carrier is comprised of a synthetic material.

5. The apparatus of claim 4, wherein:
said synthetic material is a fiber-reinforced synthetic material.

6. The apparatus of claim 1, wherein:
said carrier roller comprises means for providing resilient-mounted eccentric rotation around a rotational axis.

7. The apparatus of claim 1, further comprising:
means for restraining said driving roller from substantial movement in a longitudinal direction and a radial direction.

8. The apparatus of claim 1, wherein:
said driving roller comprises a driving surface; and
said carrier roller comprises a driven surface engageable with said driving surface of said driving roller in said driven position of said driven roller for effecting a frictional driving engagement between said driving roller and said carrier roller.

9. In an apparatus for continuous measurement of the mass of a continuously conveyed sliver, said apparatus comprising:
a driving roller rotatable about an axis of rotation;
a carrier roller positionable in a driven position with said driving roller, said carrier roller having a plurality of circumferential stepped surfaces, whereby a roller slit is defined between said driving roller and said carrier roller, through which said sliver is conveyed, said roller slit being enclosed;
a carrier upon which said carrier roller is mounted;
means for selectively
restraining at least a portion of said carrier from movement, thereby positioning said carrier roller in said driven position with said driving roller, and
facilitating movement of both said carrier and said carrier roller toward or away from said axis of rotation of said driving roller, thereby facilitating movement of said carrier roller into or out of said driven position, said means for selectively restraining at least a portion of said carrier from movement and facilitating movement of both said carrier and said carrier roller comprising at least two spaced-apart support bearings for supporting spaced-apart portions of said carrier, said carrier roller being arranged between said support bearings; and
a sensor for sensing deflections of at least a portion of said carrier roller in response to variations in the mass of said continuously conveyed sliver, wherein:
said support bearings of said carrier comprise:
a swivelling bearing for holding a first portion of said carrier and being formed by a pin within a hinge body, and
a swivelling lever and an abutment thereon, said swivelling lever being journalled for movement comprising means for enabling said lever to move from a first position, in which said abutment engages said carrier for maintaining said carrier roller in said driven position, and a second position, in which said abutment is disengaged from said carrier, thereby permitting movement of said carrier roller out of said driven position.

10. The apparatus of claim 4, wherein:
said swivelling bearing has a rotational axis which extends parallel to a line through said roller slit.

11. In an apparatus for continuous measurement of the mass of a continuously conveyed sliver, said apparatus comprising:
a driving roller rotatable about an axis of rotation;
a carrier roller positionable in a driven position with said driving roller, said carrier roller having a plurality of circumferential stepped surfaces, whereby a roller slit is defined between said driving roller and said carrier roller, through which said sliver is conveyed, said roller slit being enclosed;
a carrier upon which said carrier roller is mounted;
means for selectively
restraining at least a portion of said carrier from movement, thereby positioning said carrier roller in said driven position with said driving roller, and
facilitating movement of both said carrier and said carrier roller toward or away from said axis of rotation of said driving roller, thereby facilitating movement of said carrier roller into or out of said driven position; and
a sensor for sensing deflections of at least a portion of said carrier roller in response to variations in the mass of said continuously conveyed sliver, wherein:
said carrier comprises layers of carrier elements, said layers of carrier elements comprising at least one metallic carrier layer and at least one non-metallic carrier element layer.

12. The apparatus of claim 11, wherein:
said at least one non-metallic carrier element layer is comprised of a fiber-reinforced synthetic material.

13. In an apparatus for continuous measurement of the mass of a continuously conveyed sliver, said apparatus comprising:
a driving roller rotatable about an axis of rotation;
a carrier roller positionable in a driven position with said driving roller, said carrier roller having a plurality of circumferential stepped surfaces, whereby a roller slit is defined between said driving roller and said carrier roller, through which said sliver is conveyed, said roller slit being enclosed;
a carrier upon which said carrier roller is mounted;
means for selectively
restraining at least a portion of said carrier from movement, thereby positioning said carrier roller in said driven position with said driving roller, and facilitating movement of both said carrier and said carrier roller toward or away from said axis of rotation of said driving roller, thereby facilitating movement of said carrier roller into or out of said driven position; and a sensor for sensing deflections of at least a portion of said carrier roller in response to variations in the mass of said continuously conveyed sliver, wherein:

on both sides of said carrier roller, respective end stops are provided which are engageable with portions of said carrier facing said driving roller.

14. In an apparatus for continuous measurement of the mass of a continuously conveyed sliver, said apparatus comprising:

a driving roller rotatable about an axis of rotation;

a carrier roller positionable in a driven position with said driving roller, said carrier roller having a plurality of circumferential stepped surfaces, whereby a roller slit is defined between said driving roller and said carrier roller, through which said sliver is conveyed, said roller slit being enclosed;

a carrier upon which said carrier roller is mounted;

means for selectively
restraining at least a portion of said carrier from movement, thereby positioning said carrier roller in said driven position with said driving roller, and facilitating movement of both said carrier and said carrier roller toward or away from said axis of rotation of said driving roller, thereby facilitating movement of said carrier roller into or out of said driven position; and a sensor for sensing deflections of at least a portion of said carrier roller in response to variations in the mass of said continuously conveyed sliver, wherein:

said carrier roller comprises a running sleeve, said sleeve being rotatably held by a journal bearing on a section of a shaft connected to said carrier.

15. The apparatus of claim 14, wherein:
said running sleeve comprises recesses extending in an axial direction of said running sleeve.

16. The apparatus of claim 15, wherein:
a material for damping vibrations is provided within said recesses in said running sleeve.

17. The apparatus of claim 16, wherein:
said material for damping vibrations is plastic.

18. The apparatus of claim 16, wherein:
said material for damping vibrations is rubber.

19. In an apparatus for continuous measurement of the mass of a continuously conveyed sliver, said apparatus comprising:

a driving roller rotatable about an axis of rotation;

a carrier roller positionable in a driven position with said driving roller, said carrier roller having a plurality of circumferential stepped surfaces, whereby a roller slit is defined between said driving roller and said carrier roller, through which said sliver is conveyed, said roller slit being enclosed, and whereby said carrier roller comprises means for providing resilient-mounted eccentric rotation around a rotational axis;

a carrier upon which said carrier roller is mounted;

means for selectively
restraining at least a portion of said carrier from movement, thereby positioning said carrier roller in said driven position with said driving roller, and facilitating movement of both said carrier and said carrier roller toward or away from said axis of rotation of said driving roller, thereby facilitating movement of said carrier roller into or out of said driven position; and a sensor for sensing deflections of at least a portion of said carrier roller in response to variations in the mass of said continuously conveyed sliver, wherein:

said carrier roller comprises an inner ring and a running sleeve positioned exteriorly of said inner ring, said running sleeve having an intermediate layer comprised of a resilient material, whereby the inner ring is mounted to said carrier by means of a journal bearing.

20. The apparatus of claim 19, wherein:
said material of said intermediate layer comprises a material having a high internal damping.

21. The apparatus of claim 19, wherein:
said carrier comprises cross-sectional dimensions such that, in the event of an application of force on said carrier caused by a displacement of said running sleeve relative to said journal bearing, said carrier remains generally free from deflection.

22. An apparatus for monitoring the mass of a conveyed sliver, said apparatus comprising:

a driving roller rotatable about an axis of rotation, said driving roller having a predetermined peripheral portion;

a carrier roller rotatable about an axis of rotation and positionable in a driven position with said driving roller, said carrier roller having a predetermined peripheral portion, whereby, in said driven position of said driving roller, a slit is formed between said predetermined peripheral portion of said driving roller and said predetermined peripheral portion of said carrier roller through which said sliver is conveyed;

a carrier upon which said carrier roller is mounted, said carrier comprising a carrier portion extending from each side of said carrier roller in a direction of said axis of rotation of said carrier roller;

means for restraining each of said carrier portions from movement in a direction away from said axis of rotation of said driving roller; and means for sensing deflections of at least a portion of said carrier roller during conveyance of said sliver, wherein:

said carrier roller has a resilient portion bordering said slit, said resilient portion being deflectable under the influence of a relatively thickened section of said conveyed sliver.

23. The apparatus of claim 22, wherein:
said means for restraining each said carrier portion further comprises means for facilitating movement of both said carrier and said carrier roller toward or away from said axis of rotation of said driving roller, thereby facilitating movement of said carrier roller into or out of said driven position, respectively.

24. The apparatus of claim 22, wherein:
each of said carrier portions has a thickness and a width, said width being defined by a side generally facing said rotational axis of said driving roller, whereby each of said carrier portions comprises means for generating a greater tendency to deflect in a direction away from said rotational axis of said driving roller, under the influence of said relatively thickened section of said conveyed sliver, than in other directions.

25. The apparatus of claim 22, further comprising:
a drafting frame having conveying rollers; and
means for controlling the speed of said conveying rollers in response to signals generated by said means for sensing deflections.

26. The apparatus of claim 22, further comprising:
a carding machine having feed rollers; and
means for controlling the speed of said feed rollers in response to signals generated by said means for sensing deflections.

27. An apparatus for monitoring the mass of a conveyed sliver, said apparatus comprising:
a driving roller rotatable about an axis of rotation, said driving roller having a predetermined peripheral portion;
a carrier roller rotatable about an axis of rotation and positionable in a driven position with said driving roller, said carrier roller having a predetermined peripheral portion, whereby, in said driven position of said driving roller, a slit is formed between said predetermined peripheral portion of said driving roller and said predetermined peripheral portion of said carrier roller through which said sliver is conveyed;
a carrier upon which said carrier roller is mounted, said carrier comprising a carrier portion extending from each side of said carrier roller in a direction of said axis of rotation of said carrier roller;
a pivot bearing for supporting a first end portion of said carrier for pivoting said carrier from said driven position of said carrier roller to a displaced position for introduction of said sliver into said slit; and
a latch movable between a locked position and an unlocked position, said latch being in engagement with a second end portion of said carrier in said locked position, for maintaining said carrier roller in said driven position, and said latch being in disengagement with said second end portion of said carrier in said unlocked position, whereby, in said unlocked position of said latch, said carrier and said carrier roller are released for movement to said displaced position.

28. The apparatus of claim 27, further comprising:
means for sensing deflections of at least a portion of said carrier roller during conveyance of said sliver.

* * * * *